United States Patent [19]

Mougin

[11] Patent Number: 5,424,213
[45] Date of Patent: Jun. 13, 1995

[54] METHOD FOR TESTING THE REACTIVITY OF CELLS WITH RESPECT TO PRODUCTS

[75] Inventor: Danielle Mougin, Vitry Sur Seine, France

[73] Assignee: Laboratories De Biologie Vegetale Yves Rocher, La Gacilly, France

[21] Appl. No.: 165,342

[22] Filed: Dec. 13, 1993

[30] Foreign Application Priority Data

Dec. 24, 1992 [FR] France .................. 92 15737

[51] Int. Cl.$^6$ .................. G01N 33/50
[52] U.S. Cl. .................. 436/63; 435/7.21; 435/30; 435/39; 435/291; 435/300; 422/99
[58] Field of Search .................. 435/39, 30, 176, 284, 435/288, 291, 300, 4, 7.21, 29; 422/101, 102, 99; 436/63

[56] References Cited

U.S. PATENT DOCUMENTS

| | | | |
|---|---|---|---|
| 4,493,815 | 1/1985 | Fernwood et al. | 422/101 |
| 4,599,315 | 7/1986 | Terasaki et al. | 435/300 |
| 4,770,856 | 9/1988 | Uthemann et al. | 435/300 |
| 4,877,659 | 10/1989 | Vince | 435/300 |
| 4,956,150 | 9/1990 | Henry | 422/99 |
| 4,963,490 | 10/1990 | Churchouse et al. | 435/284 |
| 4,975,377 | 12/1990 | Key | 435/300 |
| 5,110,556 | 5/1992 | Lyman et al. | 422/102 |
| 5,130,105 | 7/1992 | Carter et al. | 422/102 |
| 5,219,528 | 6/1993 | Clark | 422/101 |
| 5,236,827 | 8/1993 | Sussman et al. | 435/4 |
| 5,264,344 | 11/1993 | Sneath | 435/300 |

FOREIGN PATENT DOCUMENTS 0128422 12/1984 European Pat. Off.
0131934 1/1985 European Pat. Off.
246173 5/1987 Germany.

OTHER PUBLICATIONS

"Quantitative assays of enzyme activity in single cells: Early prenatal diagnosis of genetic disorders", *Clinical Chemistry*, vol. 23, No. 8, Aug. 1977, Washington, D.C. pp. 1476–1484, by Hosli.

"The competitive antigen spot test (CAST) A rapid and simple means of quantitatively screening antisera", *Journal of Immunological Methods*, vol. 91, No. 1, 1986, Amsterdam, pp. 91–97, by Rozeik et al.

"Acid phosphatase staining of the stratum corneum as a marker of damage by low irritancy compounds", *British Journal of Dermatology*, vol. 91, No. 5, Nov. 1974, Oxford, pp. 503–506 by Rutherford et al.

*Primary Examiner*—Donald E. Czaja
*Assistant Examiner*—Milton I. Cano
*Attorney, Agent, or Firm*—Young & Thompson

[57] ABSTRACT

The present invention relates to a method for testing the reactivity of living cells with respect to at least one product, comprising the formation of a strip on which cells are present, application of the side of said strip on which the cells are present to the bottom of a plate containing a series of transverse openings and application of said product or products in the wells formed by the openings and the strip.

5 Claims, 1 Drawing Sheet

METHOD FOR TESTING THE REACTIVITY OF CELLS WITH RESPECT TO PRODUCTS

FIELD OF THE INVENTION

The present invention relates to a method and a device for testing the reactivity of cells with respect to at least one product. The present invention finds application, in particular, in a method for testing the reactivity of corneocytes with respect to cosmetic products.

BACKGROUND OF THE INVENTION

Before being marketed, cosmetic products have to be tested in order to verify their safety. With the object of avoiding the use of animals for such tests, ex vivo methods have been developed.

In particular, Rutherford et al. (British Journal of Dermatology, 91, 503, 1974) have proposed a method for evaluating the irritation undergone by the epidermis after treatment with marginally irritant products, and which consists in determining the presence of acid phosphatase (by the use of p-nitrophenyl phosphate) in the stratum corneum.

Hitherto, such methods could not be used industrially, since they enabled only one product to be tested at a time.

SUMMARY OF THE INVENTION

The present invention is directed towards providing a method for testing the reactivity of cells, and in particular corneocytes, with respect to several products at a time.

The subject of the present invention is also a method for testing the reactivity of cells with respect to at least one product, comprising the production or use of a strip on which cells are present, application of the side of said strip on which the cells are present to the bottom of a plate containing a series of transverse openings and application of said product or products in the wells formed by the openings and the strip.

In an advantageous form, the method according to the invention comprises, in addition, after the application of the strip to the bottom of said plate possessing openings, the application to said strip of a plate which is pressed against the strip.

Furthermore, the plate which is pressed against the strip is advantageously covered with a sheet of elastic material, such as a sheet of rubber, intended for application against the strip.

The strip used in the present invention can be a strip on which cell culturing has been performed. However, in a particular embodiment of the invention, the strip is an adhesive strip and is used to remove cells by application to a cell culture or to a human or animal organ, and is used most especially to remove human corneocytes by application to the skin.

The subject of the present invention is also a device for carrying out the method according to the invention, and which comprises a plate containing a series of transverse openings, a plate intended for application against the bottom of the plate provided with openings and means for pressing the two plates against one another.

BRIEF DESCRIPTION OF THE DRAWINGS

A better understanding of the invention will be gained in the light of the description which follows, done with reference to the attached drawings, wherein.

DETAILED DESCRIPTION OF THE INVENTION

Figure 1:
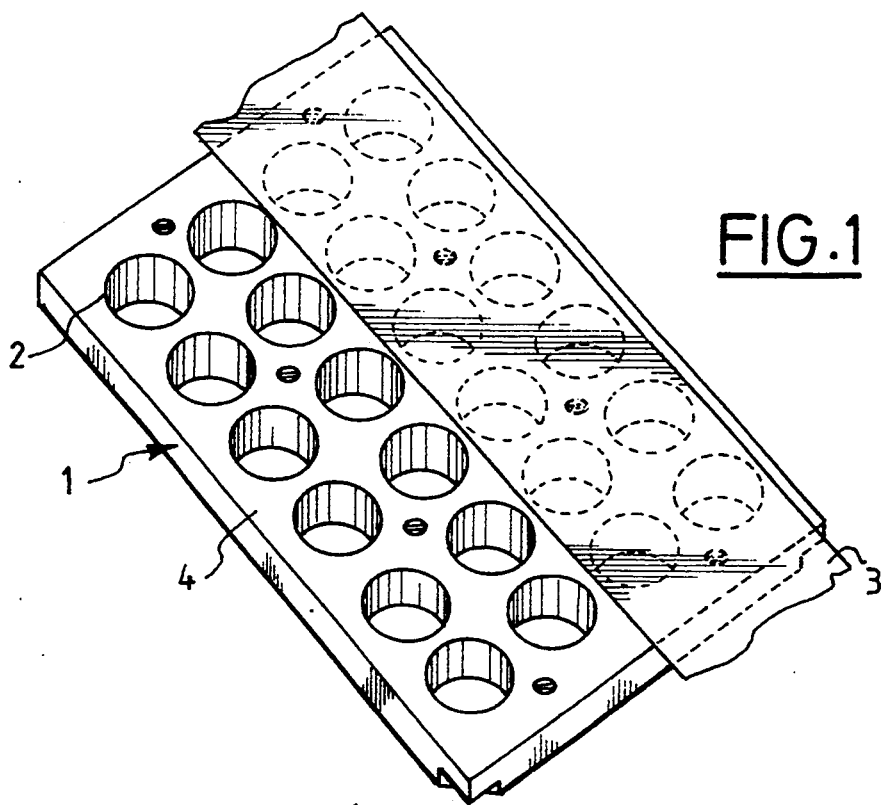
FIG. 1 is a perspective view illustrating one step of the method according to the invention.
Figure 2:
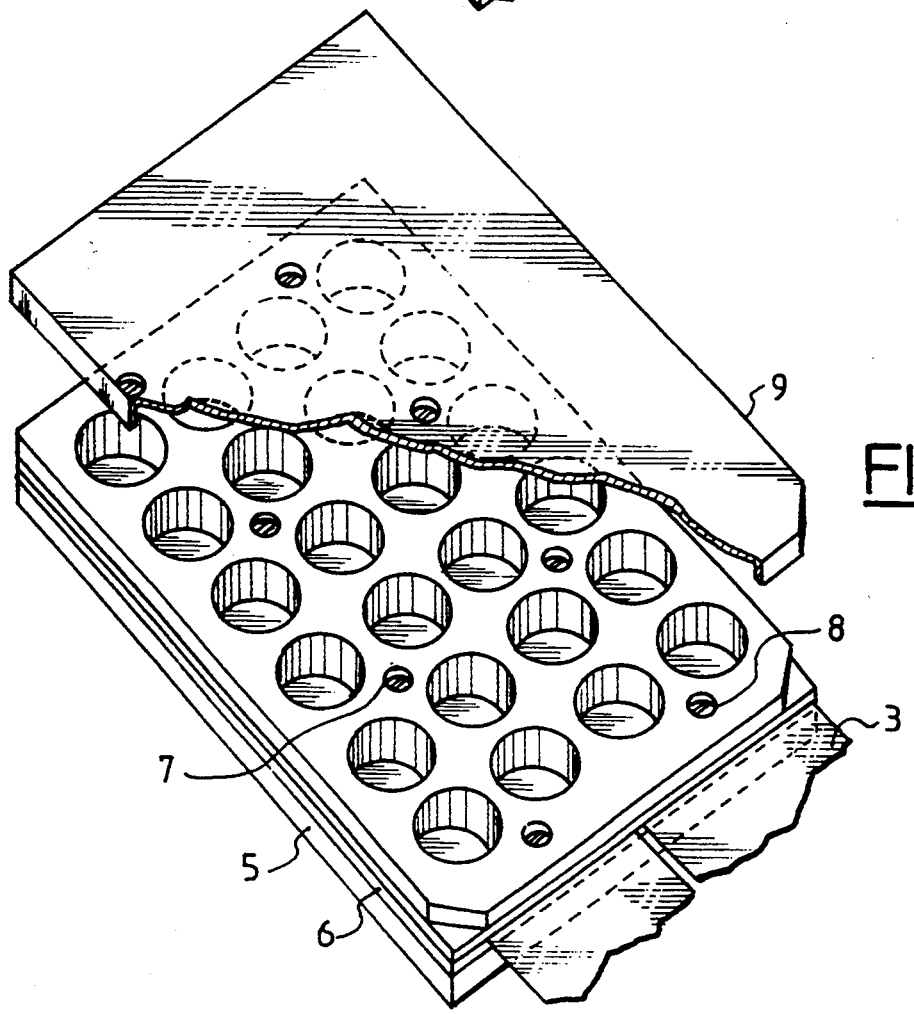
FIG. 2 is a perspective view illustrating a subsequent step of the method according to the invention.

The method which is illustrated in FIGS. 1 and 2 comprises use of a device comprising a plate 1 provided with 4 rows of transverse openings 2 possessing circular section.

An adhesive strip such as 3 is applied to the plate 1 and covers two rows of openings 2 over their entire length. The strip 3 which is applied to the plate 1 has been applied beforehand to the back of a volunteer and taken off slowly in order to remove corneocytes.

A continuous plate 5 covered on its upper face with a sheet of rubber 6 is applied to the bottom 4 of the plate 1. The whole is assembled with screws 7 introduced into drillings 8 in the plate 1 and interacting with threads sunk within the bulk of the plate 5.

Tightening of the screws 7 makes the device completely leaktight. A lid 9 enables the cells removed to be shielded from dust.

Into the different wells thus formed by the walls of the openings 2 and the adhesive strip 3, it is possible to introduce different cosmetic products or even the same cosmetic product to test the reactivity of the cells, for example of corneocytes with respect to this/these cosmetic product(s).

To this end, with wells 16 mm in diameter, 1 ml of product may be introduced per well.

The plates are incubated at the desired temperature (for example 37° C.) for the desired time (for example 2 hours).

As an example, 1 ml of a solution of p-nitrophenyl phosphate in a citrate medium was added after incubation and the preparation was left to incubate. The reaction was then stopped by adding 1 ml of 0.1M sodium hydroxide into each well.

The contents of each well are then transferred to cuvettes for a colorimetric determination at 400 nm of the acid phosphatase activity of the corneocytes.

I claim:

1. A method for testing the reactivity of living cells with respect to at least one product, comprising:
   providing a strip having a side on which the cells are present, applying the side of said strip on which the cells are present to a bottom of a plate having a series of transverse openings throughout, and applying said at least one product in wells formed by the openings and the strip so as to test the reactivity of the cells with respect to said at least one product.

2. The method as recited in claim 1, further comprising applying a second plate which is continuous and pressed against the strip, so that said strip is sandwiched between the plates.

3. The method as recited in claim 1, wherein the second plate which is pressed against the strip is covered with a sheet of elastic material.

4. The method as recited in claim 1, wherein the strip on which the cells are present is formed by removal of cells by applying an adhesive strip to a cell culture or to a human or animal organ.

5. A method for testing the reactivity of human corneocytes with respect to cosmetic products comprising:
   removing human corneocytes by applying an adhesive strip to human skin, applying said adhesive strip bearing the corneocytes to a bottom of a plate having a series of transverse openings throughout, and applying said cosmetic products in wells formed by the openings and the strip so as to test the reactivity of the corneocytes with respect to the products in said wells.

* * * * *